(12) United States Patent
Kim et al.

(10) Patent No.: US 9,393,702 B2
(45) Date of Patent: Jul. 19, 2016

(54) LINK UNIT AND ARM MODULE HAVING THE SAME

(71) Applicant: Samsung Electronics Co., Ltd., Suwon-si (KR)

(72) Inventors: Jeong Hun Kim, Suwon-si (KR); Yong Jae Kim, Seoul (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 555 days.

(21) Appl. No.: 13/772,746

(22) Filed: Feb. 21, 2013

(65) Prior Publication Data

US 2013/0213170 A1    Aug. 22, 2013

(30) Foreign Application Priority Data

Feb. 21, 2012    (KR) .......................... 10-2012-0017642

(51) Int. Cl.
| | |
|---|---|
| B25J 18/06 | (2006.01) |
| B25J 9/06 | (2006.01) |
| B25J 9/10 | (2006.01) |
| A61B 1/005 | (2006.01) |

(52) U.S. Cl.
CPC .. *B25J 18/06* (2013.01); *B25J 9/06* (2013.01); *B25J 9/104* (2013.01); *A61B 1/0055* (2013.01); *Y10T 74/20305* (2015.01)

(58) Field of Classification Search
CPC .............. B25J 18/06; B25J 9/06; B25J 9/104; A61B 1/0055; Y10T 74/20305
See application file for complete search history.

(56) References Cited

U.S. PATENT DOCUMENTS

| | | | | |
|---|---|---|---|---|
| 6,786,896 B1 * | 9/2004 | Madhani | ................ | A61B 19/22 128/898 |
| 8,025,576 B2 * | 9/2011 | Brisset | .................... | F16C 11/06 464/125 |
| 8,578,810 B2 * | 11/2013 | Donhowe | ........... | A61B 19/2203 600/141 |
| 8,666,547 B2 * | 3/2014 | Cheung | .................. | B25J 9/1617 700/248 |
| 2006/0156851 A1 * | 7/2006 | Jacobsen | .................. | B25J 18/06 74/490.01 |
| 2010/0292836 A1 * | 11/2010 | Cheung | .................. | B25J 9/1617 700/245 |
| 2010/0299101 A1 * | 11/2010 | Shimada | ................ | A61B 19/22 702/150 |
| 2011/0125165 A1 | 5/2011 | Simaan et al. | | |

(Continued)

FOREIGN PATENT DOCUMENTS

| | | |
|---|---|---|
| KR | 10-2008-0111925 | 12/2008 |
| KR | 10-2011-0036800 | 4/2011 |

*Primary Examiner* — David M Fenstermacher
(74) *Attorney, Agent, or Firm* — Harness, Dickey & Pierce, P.L.C.

(57) ABSTRACT

An arm module having a structure capable of precisely moving each link unit while flexibly moving with sufficient stiffness includes a plurality of link units each having a ring shape, a plurality of joint units each disposed in a middle portion of a corresponding one of the plurality of link units to connect the plurality of link units, wherein the plurality of link units includes a first link unit, a second link unit disposed while being rotated with respect to the first link unit, the second link unit linked at an upper side of the first link unit while passing through a middle portion of the first link unit, and a third link unit disposed while being rotated with respect to the second link unit, the third link unit linked at an upper side of the second link unit while passing through a middle portion of the second link unit.

18 Claims, 6 Drawing Sheets

(56) References Cited

U.S. PATENT DOCUMENTS

| | | | | |
|---|---|---|---|---|
| 2011/0162477 A1* | 7/2011 | Kim | B25J 9/06 | 74/490.05 |
| 2011/0218676 A1* | 9/2011 | Okazaki | B25J 9/1075 | 700/260 |
| 2011/0282359 A1* | 11/2011 | Duval | A61B 17/3423 | 606/130 |
| 2013/0165945 A9* | 6/2013 | Roelle | A61B 19/2203 | 606/130 |
| 2014/0052154 A1* | 2/2014 | Griffiths | A61B 19/2203 | 606/130 |
| 2014/0052298 A1* | 2/2014 | Hourtash | B25J 9/16 | 700/263 |
| 2014/0260755 A1* | 9/2014 | Dong | B25J 18/06 | 74/490.04 |
| 2014/0330432 A1* | 11/2014 | Simaan | B25J 9/1625 | 700/250 |
| 2015/0230697 A1* | 8/2015 | Phee | A61B 1/0125 | 600/106 |
| 2015/0245881 A1* | 9/2015 | Larkin | A61B 19/2203 | 600/424 |

* cited by examiner

LINK UNIT AND ARM MODULE HAVING THE SAME

CROSS-REFERENCE TO RELATED APPLICATIONS

This application claims the priority benefit of Korean Patent Application No. 10-2012-0017642, filed on Feb. 21, 2012 in the Korean Intellectual Property Office, the disclosure of which is incorporated herein by reference.

BACKGROUND

1. Field

The following description relates to a surgical apparatus, and more particularly, to an arm module capable of precisely moving while ensuring a sufficient stiffness thereof.

2. Description of the Related Art

In the past, an open surgery is generally performed, in which the abdomen is open for a surgery of the abdominal cavity and a surgery is carried out in a state of having the abdomen open. Because such an open surgery causes more pain and scarring while requiring more recovery time, much research has been conducted on a minimally invasive surgery (MIS).

Surgeries that are performed with minimal damage of a surgical portion of the body are commonly referred to as MIS. Examples of MIS include a laparoscopy. The laparoscopy is achieved by perforating a small incision hole into an inner part of a patient and filling gas in the inner part of the human body such that a working space is formed, and by inserting a laparoscope and a surgical instrument through the incision hole to perform a surgery. The laparoscopy is also referred to as a multi port surgery due to the fact that the surgery forms a plurality of incision holes.

The laparoscopy has a large number of benefits when compared to the open surgery, but because a plurality of incision holes are formed, laparoscopy still has some of the constraints associated with the open surgery.

Accordingly, many studies have been undertaken recently on a single port surgery that uses a single incision hole and a natural orifice transluminal endoscopic surgery (NOTES) that uses no incision hole.

The NOTES is performed by allowing an arm module to be inserted into a natural orifice, such as a mouth or an anus, and to approach a surgical portion of the body such that a surgery is conducted using a surgery instrument installed at an end portion of the arm module.

However, when the single port surgery or the NOTES is performed, the arm module is needed to pass along the internal part or the intestines of the patient that have curves, and also is needed to support the surgery instrument while being firmly fixed at the surgical portion.

SUMMARY

Therefore, it is an aspect of the present disclosure to provide an arm module having a structure capable of precisely moving each link unit while flexibly moving with a sufficient stiffness.

It is an aspect of the present disclosure to provide an arm module capable of transmitting a driving force afar with a driving apparatus.

Additional aspects of the disclosure will be set forth in part in the description which follows and, in part, will be obvious from the description, or may be learned by practice of the disclosure.

In accordance with an aspect of the present disclosure, an arm module includes a plurality of link units and a plurality of joint units. The plurality of link units each may have a ring shape. The plurality of joint units each may be disposed in a middle portion of a corresponding one of the plurality of link units to connect the plurality of link units to one another. The plurality of link units may include a first link unit, a second link unit, and a third link unit. The second link unit may be disposed while being rotated with respect to the first link unit, the second link unit linked at an upper side of the first link unit while passing through a middle portion of the first link unit. The third link unit may be disposed while being rotated with respect to the second link unit, the third link unit linked at an upper side of the second link unit while passing through a middle portion of the second link unit.

The first link unit and the third link unit may be disposed while making contact with each other.

Each of the plurality of link units may include a main frame and a toothed part. The main frame may form an external appearance of the link unit. The toothed part may be formed at an upper end portion and a lower end portion of the main frame.

The toothed part may be provided with a cross section having a toothed shape.

The first link unit and the third link unit may be disposed such that a toothed part formed at an upper end portion of the first link unit makes contact with a toothed part formed at a lower end portion of the third link unit.

Each of the plurality of link units may include a plurality of protrusions and a plurality of through-holes. The plurality of protrusions may protrude to a lateral side from the main frame. The plurality of through-holes may be formed at each of the plurality of protrusions, and allow a cable, which is configured to rotate the link unit, to pass therethrough.

The plurality of through-holes of the first link unit may be disposed in line with the plurality of through-holes of the second link unit that is disposed while being rotated with respect to the first link unit.

Each of the plurality of link units may further include a mounting hole. The mounting hole may be provided at the main frame, and configured to allow the joint unit to be mounted therethrough.

The plurality of mounting holes may include an upper mounting hole and a lower mounting hole that are provided at an upper portion and a lower portion of the main frame, respectively.

The joint unit may include an upper joint unit and a lower joint unit. The upper joint unit may be mounted at the upper mounting hole. The lower joint unit may be mounted at the lower mounting hole.

The joint unit may include a main body and a coupling bar. The coupling bar may be configured to couple the joint unit to the link unit while being coupled to the main body.

The coupling bar may be coupled to the main body while passing through the mounting hole.

In accordance with an aspect of the present disclosure, an arm module includes a plurality of link units and a plurality of joint units. The plurality of link units each may have a ring shape. The plurality of joint units each may be disposed in a middle portion of a corresponding one of the plurality of link units to connect the plurality of link units to one another. Two link units, which are adjacent to each other among the plurality of link units, may be linked with each other such that the two link units are disposed while being rotated with respect to each other.

The joint unit may be disposed between the two link units, which are adjacent to each other, among the plurality of link units to guide a rotation of the two link units.

In accordance with an aspect of the present disclosure, an arm module formed by linking a plurality of link units each having a ring shape with one another is provided. The plurality of link units may include a first link unit, a second link unit linked with an upper side of the first link unit, and a third link unit linked with a lower side of the first link unit. Each of the plurality of link units may include a main frame forming an external appearance of the link unit, and a toothed part formed at an upper end portion and a lower end portion of the main frame. A toothed part formed at a lower end portion of the second link unit may be disposed to be engaged with a toothed part formed at an upper end portion of the third link unit.

The first link unit and the second link unit may be disposed to be linked while being disposed to be rotated with respect to each other. The first link unit and the third link unit may be disposed to be linked while being disposed to be rotated with respect to each other.

In accordance with an aspect of the present disclosure, a link unit includes a main frame and a toothed part. The main frame may have a middle portion thereof open in a ring shape to form an opening. The toothed part may be formed at an upper end portion and a lower end portion of the main frame.

The opening formed in the middle portion of the main frame may be provided in an oval shape.

The link unit may further include a plurality of protrusions and a plurality of through-holes. The plurality of protrusions may protrude toward a lateral side from the main frame. The plurality of through-holes may be formed at an end portion of each of the plurality of protrusions.

As described above, the arm module may flexibly move due to a link structure of each link unit and a joint unit while ensuring a sufficient stiffness.

Due to a toothed part of the link unit, the link unit which is spaced apart from the driving part precisely moves to a degree desired by a user.

BRIEF DESCRIPTION OF THE DRAWINGS

These and/or other aspects of the disclosure will become apparent and more readily appreciated from the following description of the embodiments, taken in conjunction with the accompanying drawings of which.

DETAILED DESCRIPTION

Figure 1:
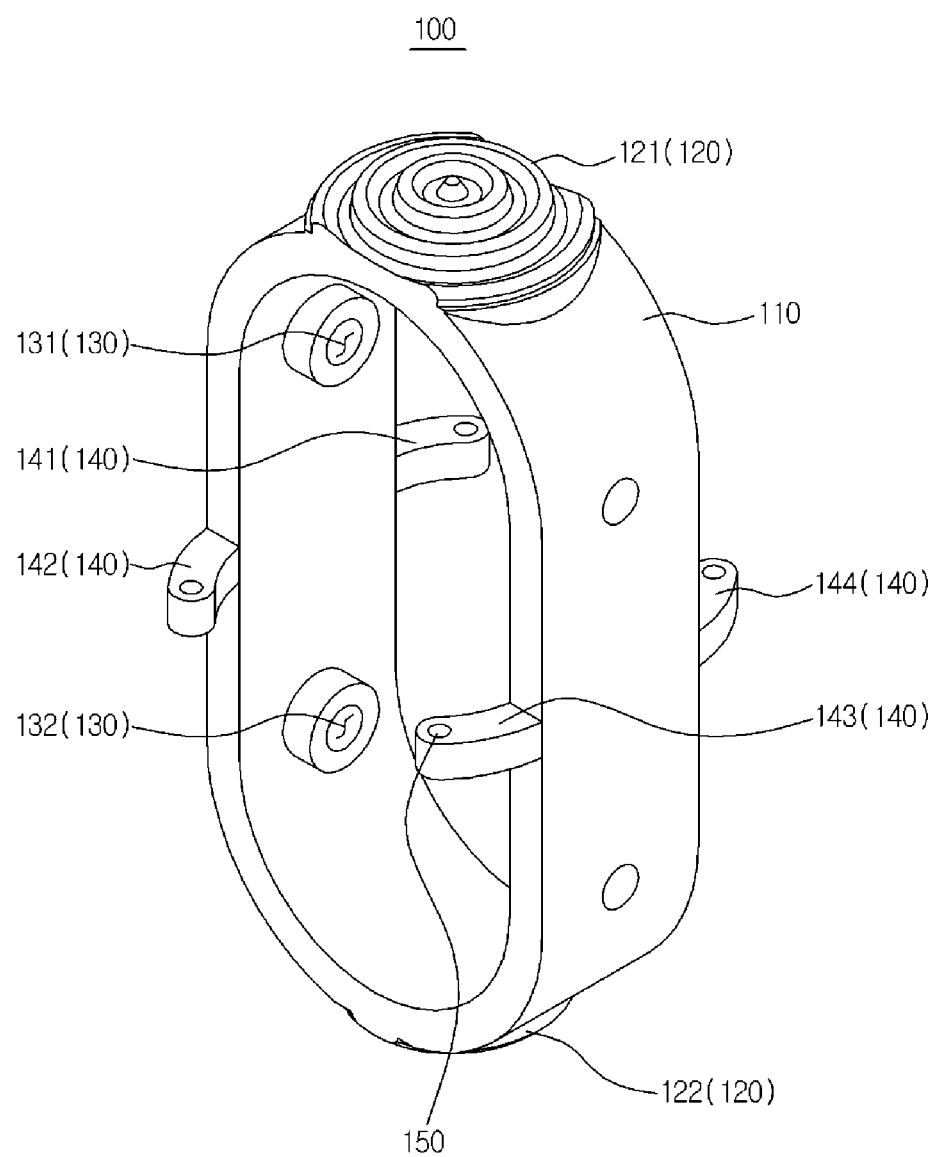
FIG. 1 is a view illustrating a link unit in accordance with an embodiment of the present disclosure.

Reference will now be made in detail to the embodiments of the present disclosure, examples of which are illustrated in the accompanying drawings, wherein like reference numerals refer to like elements throughout.

FIG. 1 is a view illustrating a link unit in accordance with an embodiment of the present disclosure.

Referring to FIG. 1, a link unit 100 includes a main frame 110 that forms the external appearance of the link unit 100. The main frame 110 has a middle portion thereof open in a ring shape to form an opening.

The main frame 110 shown on the drawings is illustrated as having a vertical length longer than a horizontal length. An upper end and a lower end of the main frame 110 are rounded. The shape of the main frame 110 shown on FIG. 1 is illustrated as an example of the shape of the main frame 110. In a case that the main frame 110 is provided at a middle portion thereof with an opening formed therethrough in a shape of a ring, the ring may have an oval shape or a circular shape.

Figure 4:
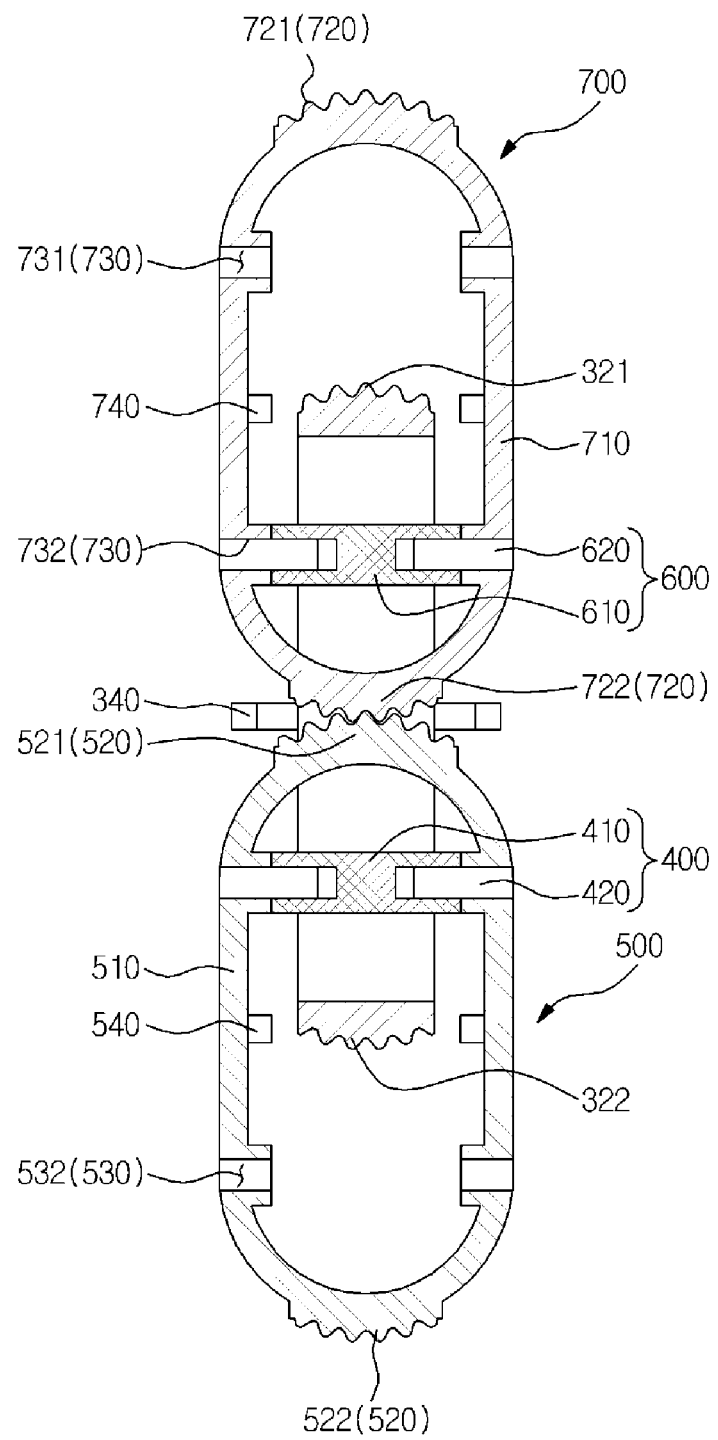
FIG. 4 is a cross sectional view illustrating a coupling relation among three link units of the arm module of the present disclosure.

A toothed part 120 may be formed at an upper end portion, as toothed part 121, of the main frame 110 and a lower end portion, as toothed part 122, of the main frame 110. The toothed part 120 is provided with a plurality of teeth that protrude at the upper end portion and the lower end portion of the main frame 110. The plurality of teeth is each provided in a circular shape while having different heights from one another. Referring to FIG. 4, the toothed part 120 formed by the plurality of teeth is provided in a shape of sawteeth.

A plurality of protrusions 140 may be formed while protruding from a lateral side of the main frame 110. A through-hole 150 may be formed through an end portion of each of the plurality of protrusions 140. A cable (not shown) configured to adjust an arm module 10 passes through the through-hole 150.

The plurality of protrusions 140 is provided in two pairs of protrusions, that is, a total of four protrusions, so that the arm module 10 formed by the plurality of link units 100 is provided with two degrees of freedom.

The main frame 110 may be provided with a mounting hole 130 that allows a joint unit (400 in FIG. 2), which is to be described later, to be mounted thereon. Because a total of two joint units are installed at each link unit 110, the mounting hole 130 is provided with one pair of mounting holes 130 at each of the upper portion and the lower portion of the main frame 110. That is, the mounting hole 130 includes an upper mounting hole 131 and a lower mounting hole 132.

Figure 2:
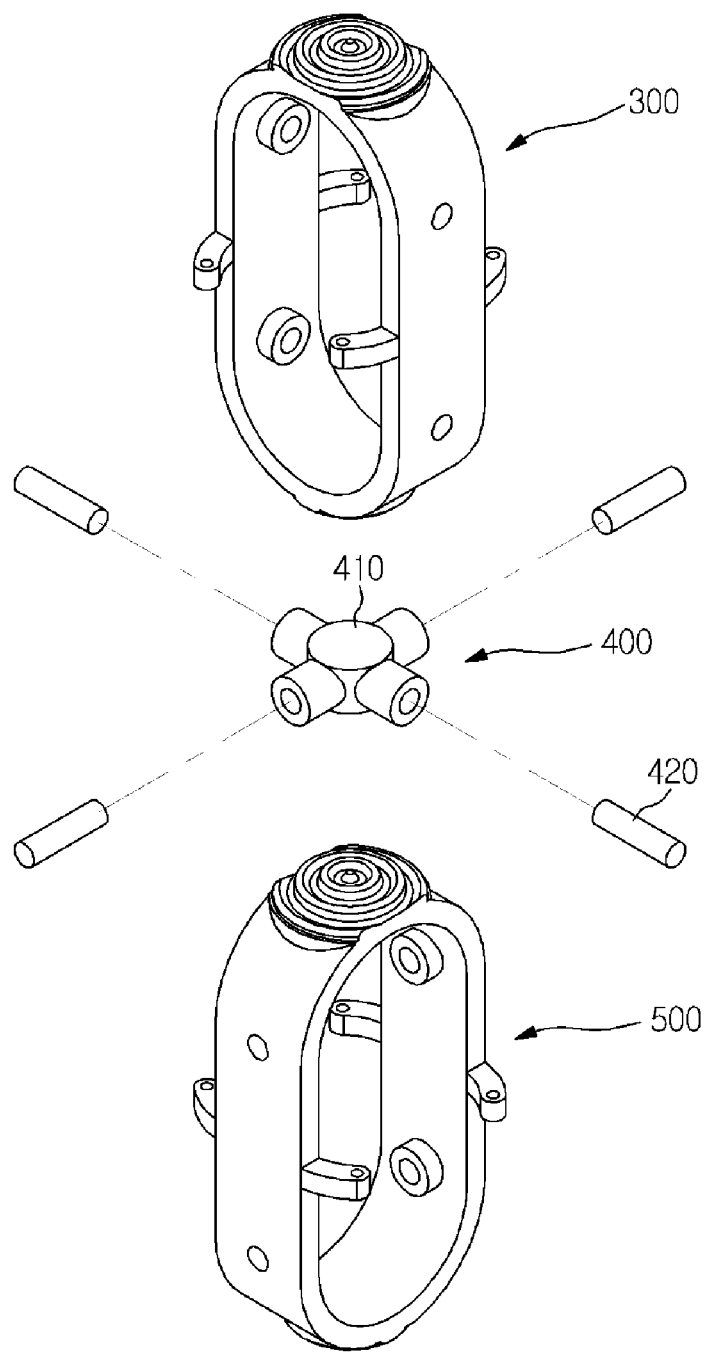
FIG. 2 is an exploded perspective view illustrating a coupling relation between two link units of an arm module in accordance with an embodiment of the present disclosure.
Figure 3:
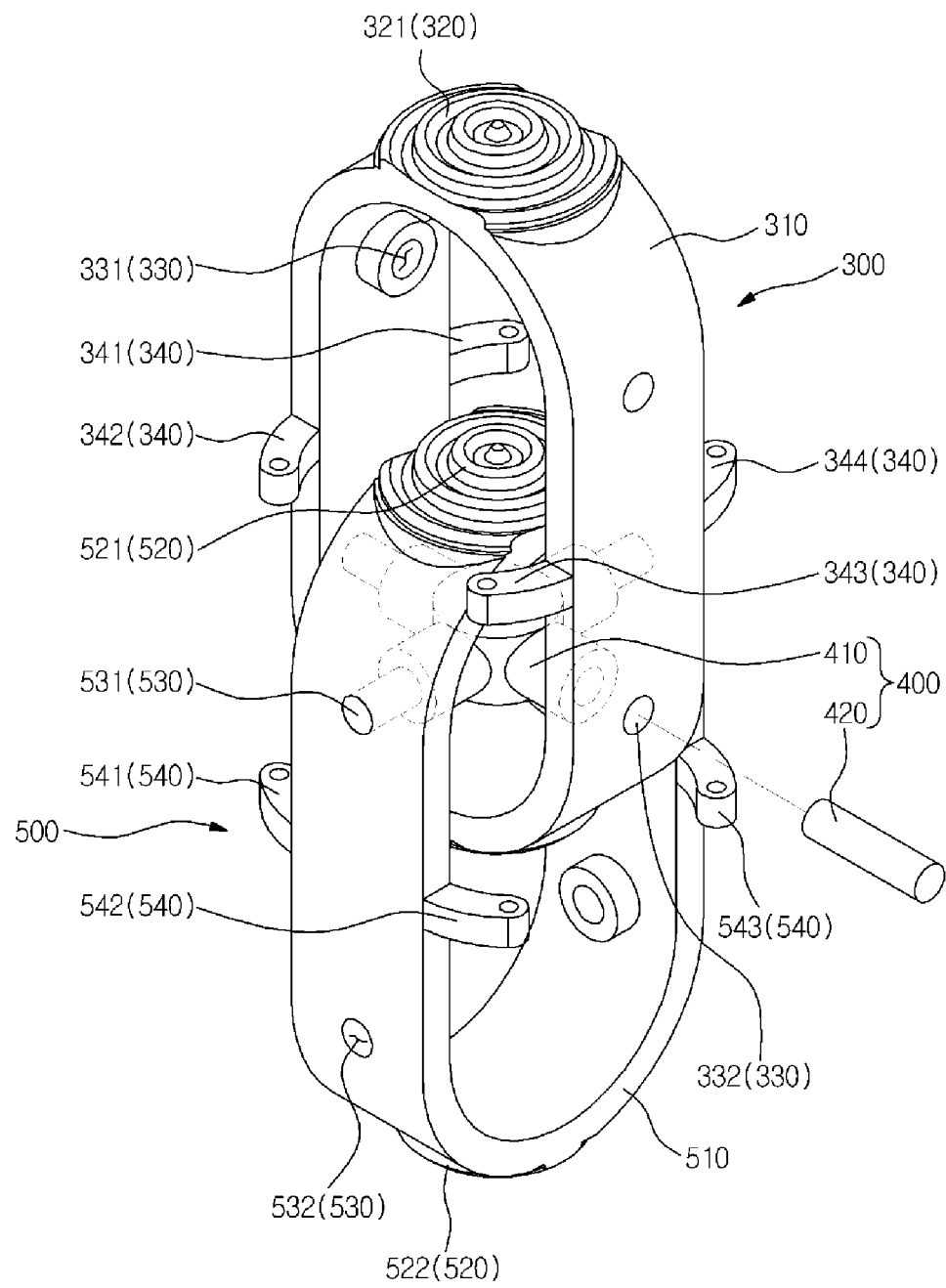
FIG. 3 is a view illustrating a coupling relation between the two link units of the arm module of FIG. 2.

FIG. 2 is an exploded perspective view illustrating a coupling relation between two link units of an arm module in accordance with an embodiment of the present disclosure. FIG. 3 is a view illustrating a coupling relation between the two link units of the arm module of FIG. 2.

Referring to FIGS. 2 and 3, a first link unit 300 is disposed at an upper side and a second link unit 500 is disposed at a lower side of the first link unit 300. The joint unit 400 configured to connect the first link unit 300 to the second link unit 500 is disposed between the first link unit 300 and the second link unit 500.

The joint unit 400 includes a main body 410 that forms the external appearance of the joint unit 400. Coupling bars 420 are coupled to each side of the main body 400. The coupling bars 420 are provided in a size and a shape corresponding to a size and a shape of the mounting holes 330 and 530 of the first link unit 300 and the second link unit 500 to be suitable for being coupled to the mounting holes 330 and 530 of the first link unit 300 and the second link unit 500, respectively.

First, the main body 410 of the joint unit 400 is disposed between the first link unit 300 and the second link unit 500, and then the coupling bar 420 is coupled to the main body 410 by passing through the mounting holes 330 and 530, so that the joint unit 400 is assembled while coupling the first link unit 300 to the second link unit 500.

In the embodiment of the present disclosure, for the sake of convenience, the coupling bar 420 and the main body 410 are separately provided from each other. However, having the coupling bar 420 integrally formed with the main body 410 may be included in the aspect of the present disclosure.

A toothed part 320 may be formed at an upper end portion, as toothed part 321, of the main frame 310 and a lower end portion, as toothed part 322, of the main frame 310. A toothed part 520 may be formed at an upper end portion, as toothed part 521, of the main frame 510 and a lower end portion, as toothed part 522, of the main frame 510.

The first link unit 300 is connected to the second link unit 500 as a main frame 310 of the first link unit 300 passes through an opening of a main frame 510 of the second link unit 500 while the main frame 510 of the second link unit 500 passes through an opening of the main frame 310 of the first link unit 300. The first link unit 300 and the second link unit 500 are linked with each other to be disposed while being rotated with respect to each other at an angle of 90 degrees. Although the first link unit 300 and the second link unit 500 in accordance with an embodiment of the present disclosure have been illustrated as being linked while being rotated with respect to each other at an angle of 90 degrees, the present disclosure is not limited thereto. According to an embodiment of the present disclosure, the first link unit 300 and the second link unit 500 may be linked while being rotated with respect to each other at a different angle.

The joint unit 400 is disposed between the first link unit 300 and the second link unit 500. The joint unit 400 allows two of the coupling bars 420 to be disposed and mounted at lower mounting holes 332 of the first link unit 300 while allowing the remaining two of the coupling bars 420 to be disposed and mounted at upper mounting holes 531 of the second link unit 500. That is, the first link unit 300 is connected to the second link unit 500 such that the lower mounting hole 332 of the first link unit 300 is disposed to be coplanar with the upper mounting hole 531 of the second link unit 500. The second link unit 500 further includes lower mounting hole 532.

The joint unit 400, while connecting the first link unit 300 to the second link unit 500, may guide the rotating direction of the first link unit 300 and the second link unit 500 when the first link unit 300 and the second link unit 500 rotate relative to each other. The first link unit 300 and the second link unit 500 may rotate in a first direction while having one pair of coupling bars 420 mounted at the lower mounting hole 332 of the first link unit 300 as an axis of rotation. Additionally, the first link unit 300 and the second link unit 500 may rotate in a second direction perpendicular to the first direction while having one pair of coupling bars 420 mounted at the upper mounting hole 531 of the second link unit 500 as an axis of rotation.

Because the cable (not shown) passes through the through-holes 150 of protrusions 340 and 540, the protrusion 340 of the first link unit 300 and the protrusion 540 of the second link unit 500 are formed such that the through-hole 150 of the protrusion 340 of the first link unit 300 is disposed in line with the through-hole 150 of the protrusion 540 of the second link unit 500.

That is, the through-holes 150 of a first protrusion 341, a second protrusion 342, a third protrusion 343, and a fourth protrusion 344 of the first link unit 300 are disposed in line with the through-holes 150 of a fourth protrusion (not shown), a first protrusion 541, a second protrusion 542, and a third protrusion 543 of the second link unit 500, respectively.

As described above, because the link units 300 and 500 are connected to each other through the joint unit 400, the first link unit 300 and the second link unit 500 are firmly coupled to each other, and the arm module 10 formed by the link units 300 and 500 has a sufficient stiffness. In addition, because the link unit 100 rotates while having the coupling bar 420 of the joint unit 400 as an axis of rotation, the link unit 100 may flexibly rotate, thereby enabling a natural movement of the arm module 10.

FIG. 4 is a cross sectional view illustrating a coupling relation among three link units of the arm module of the present disclosure.

Referring to FIG. 4, the first link unit 300, the second link unit 500, and a third link unit 700 are connected to one another.

The second link unit 500 is disposed at a lower side of the first link unit 300, and the third link unit 700 is disposed at an upper side of the first link unit 300.

The second link unit 500 and the third link unit 700 are disposed while passing through the opening of the main frame 310 of the first link unit 300. In addition, the second link unit 500 and the third link unit 700 may be disposed while being rotated with respect to the first link unit 300 at an angle of 90 degrees. Accordingly, the second link unit 500 and the third link unit 700 are disposed such that the main frame 510 of the second link unit 500 and the main frame 710 of the third link unit 700 face the same direction.

The first link unit 300 is connected to the second link unit 500 through the first joint unit 400. The first joint unit 400 may be coupled to the lower mounting hole 132 of the first link unit 300 and the upper mounting hole 331 of the second link unit 500.

The first link unit 300 is connected to the third link unit 700 through a second joint unit 600. The third joint unit 700 may include mounting holes 730, including upper mounting hole 731 and lower mounting hole 732, and a plurality of protrusions 740. The second joint unit 600 may be coupled to the upper mounting hole 131 of the first link unit 300 and the lower mounting hole 732 of the third link unit 700. The second joint unit 600 may include a main body 610 and a coupling bar 620.

A toothed part 720 may be formed at an upper end portion, as toothed part 721, of the main frame 710 and a lower end portion, as toothed part 722, of the main frame 710.

The upper toothed part 521 of the second link unit 500 is disposed to be engaged with the lower toothed part 722 of the third link unit 700. Because the second link unit 500 is connected to the third link unit 700 as the upper toothed part 521 of the second link unit 500 is engaged with the lower toothed part 722 of the third link unit 700, the link units 500 and 700 rotate at a precise position. That is, while preventing the link units 500 and 700 from being slid against each other, the link units 500 and 700 rotate at a desired angle.

In addition, because the second link unit 500 and the third link unit 700 are rotated in a state of the toothed parts 521 and 722 engaged with each other, a force of pushing or relaxing, or pulling the link units 300, 500, and 700 by a driving part (not shown) is easily transmitted up to the third link unit 700. Further, the driving force generated by the driving part (not shown) is easily transmitted to another link unit that is to be connected to an upper side of the third link unit 700.

Figure 5:
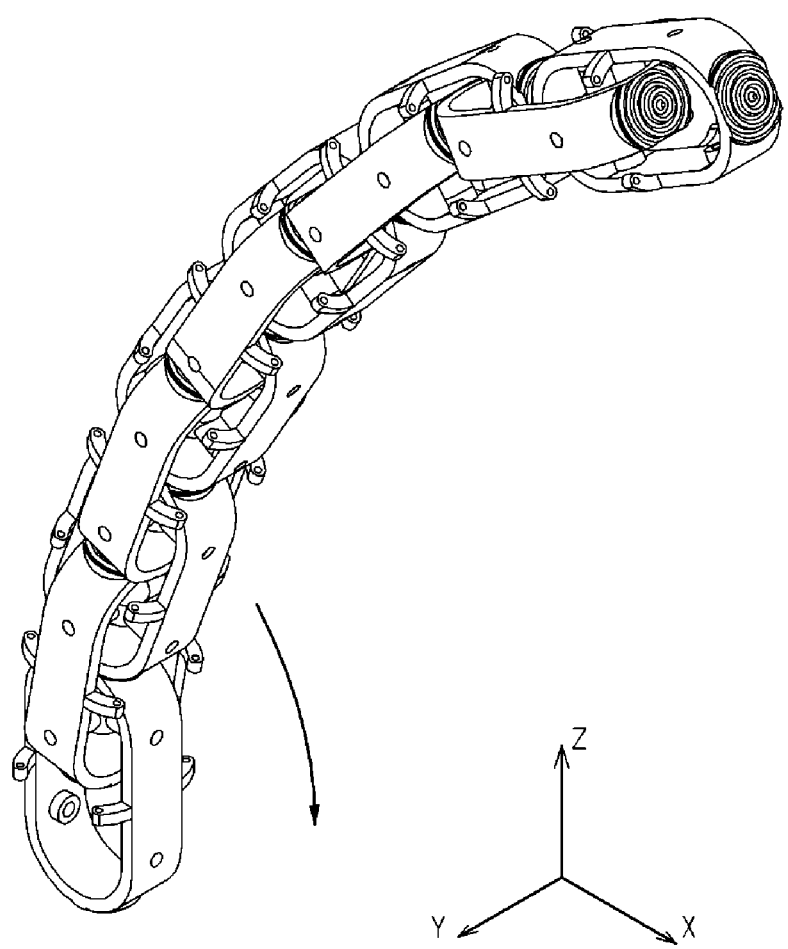
FIGS. 5 and 6 are views illustrating an operation of the arm module in accordance with the embodiment of the present disclosure.
Figure 6:
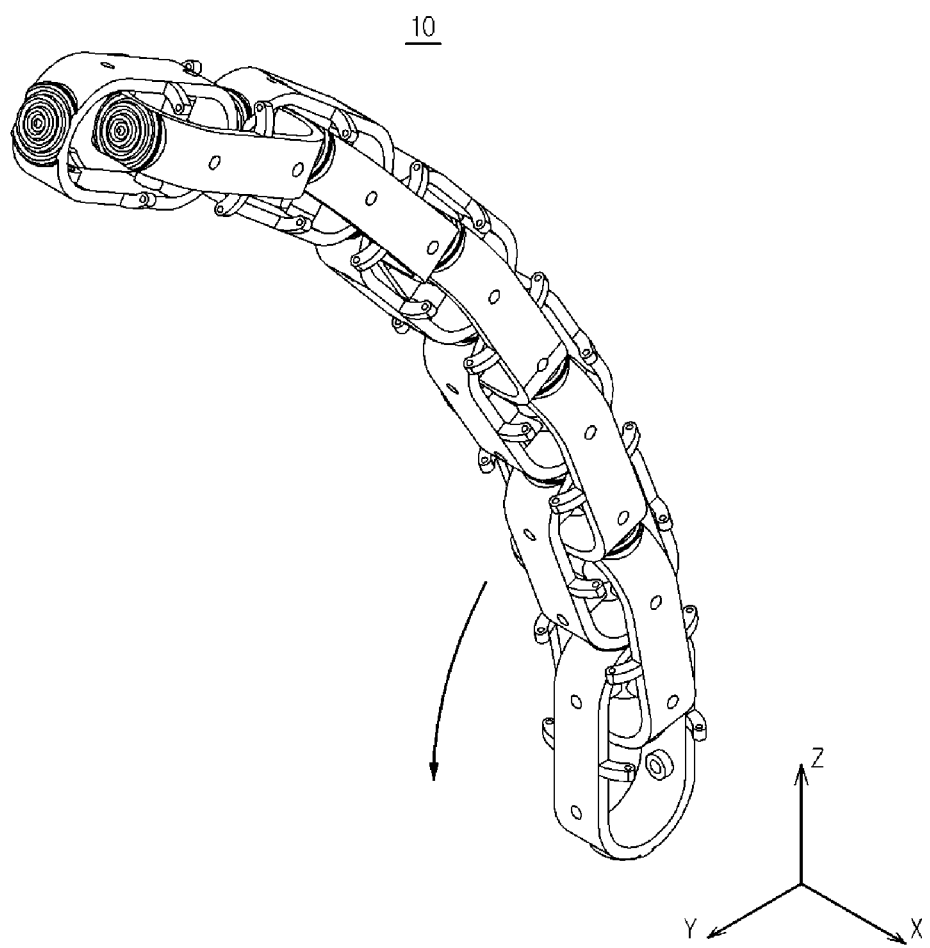

FIGS. 5 and 6 are views illustrating an operation of the arm module in accordance with an embodiment of the present disclosure.

FIG. 5 is a view illustrating the arm module 10 rotating with respect to the X-axis. The following operation will be described while assuming that a link unit disposed at the lower-most portion is the link unit 100 shown on FIG. 1.

Referring to FIGS. 1 and 5, the arm module 10 is formed by connecting a plurality of link units 100 to one another.

The description of the connection structure of the link unit 100 is substituted with that of the connection structure described above.

If a pair of cables (not shown), each disposed to pass through the through-hole 150 of a third protrusion 143 and the through-hole 150 of a fourth protrusion 144 of the link unit 100, is pulled while pushing or relaxing a pair of cables (not shown) each disposed to pass through the through-hole 150 of a first protrusion 141 and the through-hole 150 of a second protrusion 142 of the link unit 100 is pushed or relaxed, the arm module 10 rotates with respect to the X-axis.

Because the arm module 10 rotate in a state that the toothed parts 120 in between the plurality of link units 100 are engaged with each other, the link units 100 rotate at a precise angle. In addition, the driving force is effectively transmitted from the link unit 100 disposed at the lower-most portion to the link unit 100 disposed at the upper-most portion.

On the contrary, If a pair of cables (not shown), each disposed to pass through the through-hole 150 of the third protrusion 143 and the through-hole 150 of the fourth protrusion 144, is pushed or relaxed while pulling a pair of cables (not shown), each disposed to pass through the through-hole 150 of the first protrusion 141 and the through-hole 150 of the second protrusion 142, is pulled, the arm module 10 rotates with respect to the negative X-axis.

FIG. 6 is a view illustrating the arm module 10 rotating with respect to the Y-axis.

Referring to FIGS. 1 and 6, if a pair of cables (not shown) each disposed to pass through the through-hole 150 of the second protrusion 142 and the through-hole 150 of the third protrusion 143 of the link unit 100 is pulled while pushing or relaxing a pair of cables (not shown) each disposed to pass through the through-hole 150 of the first protrusion 141 and the through-hole 150 of the fourth protrusion 144 is pushed or relaxed, the arm module 10 rotates with respect to the Y-axis.

On the contrary, if a pair of cables (not shown) each disposed to pass through the through-hole 150 of the second protrusion 142 and the through-hole 150 of the third protrusion 143 is pushed or relaxed while pushing or relaxing a pair of cables (not shown) each disposed to pass through the through-hole 150 of the first protrusion 141 and the through-hole 150 of the fourth protrusion 144 is pulled, the arm module 10 rotates with respect to the negative Y-axis.

Through the proper adjustment as shown on FIGS. 5 and 6, the arm module 10 may move in a direction that is not restricted.

Although the arm module 10 in accordance with the embodiment of the present disclosure is provided in a total of one arm module, the present disclosure is not limited thereto. A surgical apparatus may be formed by using a plurality of arm modules 10. In a case where the plurality of arm modules 10 is coupled, each arm module moves with an individual degree of freedom, so that the surgical apparatus including the plurality of arm modules 10 may pass through a curved path without restriction.

Although a few embodiments of the present disclosure have been shown and described, it would be appreciated by those skilled in the art that changes may be made in these embodiments without departing from the principles and spirit of the disclosure, the scope of which is defined in the claims and their equivalents.

What is claimed is:

1. An arm module comprising:
 a plurality of link units each having a ring shape; and
 a plurality of joint units each in a middle portion of a corresponding one of the plurality of link units to connect the plurality of link units to one another, the plurality of link units including,
  a first link unit,
  a second link unit being rotated with respect to the first link unit, the second link unit linked at an upper side of the first link unit while passing through a middle portion of the first link unit, and
  a third link unit being rotated with respect to the second link unit, the third link unit linked at an upper side of the second link unit while passing through a middle portion of the second link unit, wherein
 each of the plurality of link units include a main frame, and a toothed part formed at an upper end portion and a lower end portion of the main frame.

2. The arm module of claim 1, wherein the first link unit and the third link unit contact each other.

3. The arm module of claim 1, wherein a cross section of the toothed part has a toothed shape.

4. The arm module of claim 3, wherein the toothed part at an upper end portion of the first link unit contacts the toothed part at a lower end portion of the third link unit.

5. The arm module of claim 1, wherein each of the plurality of link units comprises:
 a plurality of protrusions protruding from a lateral side of the main frame; and
 a plurality of through-holes formed at each of the plurality of protrusions, and allowing a cable, which is configured to rotate the link unit, to pass therethrough.

6. The arm module of claim 5, wherein the plurality of through-holes of the first link unit is in line with the plurality of through-holes of the second link unit while being rotated with respect to the first link unit.

7. The arm module of claim 6, wherein each of the plurality of link units further comprises:
 a mounting hole provided at the main frame, and configured to allow the joint unit to be mounted therethrough.

8. The arm module of claim 7, wherein the plurality of mounting holes comprises a upper mounting hole and a lower mounting hole that are provided at an upper portion and a lower portion of the main frame, respectively.

9. The arm module of claim 8, wherein the joint unit comprises an upper joint unit mounted at the upper mounting hole, and a lower joint unit mounted at the lower mounting hole.

10. The arm module of claim 7, wherein the joint unit comprises a main body, and a coupling bar configured to couple the joint unit to the link unit while being coupled to the main body.

11. The arm module of claim 9, wherein the coupling bar is coupled to the main body while passing through the mounting hole.

12. An arm module comprising:
 a plurality of link units each having a ring shape; and
 a plurality of joint units each in a middle portion of a corresponding one of the plurality of link units to connect the plurality of link units to one another, wherein
  two link units, which are adjacent to each other, among the plurality of link units are linked with each other such that the two link units are rotated with respect to each other, and
 each of the two link units include a main frame, and a toothed part formed at an upper end portion and a lower end portion of the main frame.

13. The arm module of claim 12, wherein the joint unit is between the two link units, which are adjacent to each other, among the plurality of link units to guide a rotation of the two link units.

14. An arm module comprising:
 a plurality of link units linked together, each of the plurality of link units having a ring shape, wherein
 the plurality of link units include,
  a first link unit,
  a second link unit linked with an upper side of the first link unit, and
  a third link unit linked with a lower side of the first link unit, each of the first link unit, the second link unit and the third link unit have a main frame, and a toothed part formed at an upper end portion and a lower end portion of the main frame, and the toothed part formed at a lower end portion of the second link unit is configured to engage with the toothed part at an upper end portion of the third link unit.

15. The arm module of claim 14, wherein:

the first link unit and the second link unit are linked while being rotatable with respect to each other, and the first link unit and the third link unit linked while being rotatable with respect to each other.

16. A first link unit comprising:

a main frame having a middle portion thereof open in a ring shape to form an opening; and a toothed part at an upper end portion and a lower end portion of the main frame, wherein the first link unit is configured to link, via a joint unit in the middle portion, to a second link unit to form an arm module such that the first link unit and the second link unit are configured to rotate with respect to each other.

17. The first link unit of claim 16, wherein the opening formed in the middle portion of the main frame is provided in an oval shape.

18. The first link unit of claim 16, further comprising:

a plurality of protrusions protruding toward a lateral side from the main frame; and a plurality of through-holes formed at an end portion of each of the plurality of protrusions.

\* \* \* \* \*